United States Patent [19]

Andersson et al.

[11] Patent Number: 5,258,162

[45] Date of Patent: Nov. 2, 1993

[54] METHOD OF PRODUCING A GASEOUS HYDROGEN PEROXIDE-CONTAINING STERILIZATION FLUID

[75] Inventors: Jan Andersson, Ystad; Lars Martensson, Malmö; Thomas Bjerborn; Göran Smith, both of Lund, all of Sweden

[73] Assignee: Tetra Alfa Holdings S.A., Pully, Switzerland

[21] Appl. No.: 921,594

[22] Filed: Jul. 31, 1992

Related U.S. Application Data

[63] Continuation of Ser. No. 605,409, Oct. 30, 1990, abandoned.

[30] Foreign Application Priority Data

Nov. 7, 1989 [SE] Sweden .................................. 8903720

[51] Int. Cl.$^5$ ......................... A61L 2/00; B65B 55/02
[52] U.S. Cl. ..................................... 422/28; 422/292; 422/302; 422/306; 53/425
[58] Field of Search ....................... 422/27, 28, 29, 30, 422/32, 292, 297, 298, 300, 302, 304, 306; 53/425, 426

[56] References Cited

U.S. PATENT DOCUMENTS

| | | | |
|---|---|---|---|
| 3,637,977 | 1/1972 | Folke | 422/28 |
| 4,447,394 | 5/1984 | Krouthen | 422/27 |
| 4,511,538 | 4/1985 | Buchner et al. | 422/303 |
| 4,512,935 | 4/1985 | Hilmersson et al. | 261/79 A |
| 4,633,594 | 1/1987 | Bovone | 34/48 |
| 4,734,268 | 3/1988 | Redding et al. | 422/292 |
| 4,742,667 | 5/1988 | Müller et al. | 53/167 |
| 4,797,255 | 1/1989 | Hatanaka et al. | 422/28 |
| 4,909,999 | 3/1990 | Cummings et al. | 422/298 |
| 4,992,247 | 2/1991 | Foti | 422/304 |

FOREIGN PATENT DOCUMENTS

| | | |
|---|---|---|
| 33362/89 | 11/1989 | Australia . |
| 0139536 | 5/1985 | European Pat. Off. . |
| 0321908 | 6/1989 | European Pat. Off. . |
| 0384535 | 8/1990 | European Pat. Off. . |
| WO86/02712 | 5/1986 | PCT Int'l Appl. . |
| 743565 | 6/1980 | U.S.S.R. . |
| 2183480A | 6/1987 | United Kingdom . |

Primary Examiner—Robert J. Warden
Assistant Examiner—T. A. Trembley
Attorney, Agent, or Firm—Burns, Doane, Swecker & Mathis

[57] ABSTRACT

A method of producing a gaseous, hydrogen peroxide-containing sterilization fluid displaying good, uniform sterilization properties is disclosed. The method includes vaporizing liquefied hydrogen peroxide by injecting the liquefied hydrogen peroxide intermittently in finely-divided form into an air current which serves as a vaporization agent, wherein the air current is kept at a constant or insignificantly varying elevated vaporization temperature. An even vaporization temperature of the air current is ensured because the air, prior to vaporization, is heated by heat exchange with a heating element having a large mass or thermal capacity and a large heat exchange surface area which is kept at the desired elevated temperature by regulated energy supplied to the heating element. During breaks in vaporization between the intermittent injection of the liquefied hydrogen peroxide, the heat exchange surface area is heated with the aid of heat stored in the heating element.

6 Claims, 3 Drawing Sheets

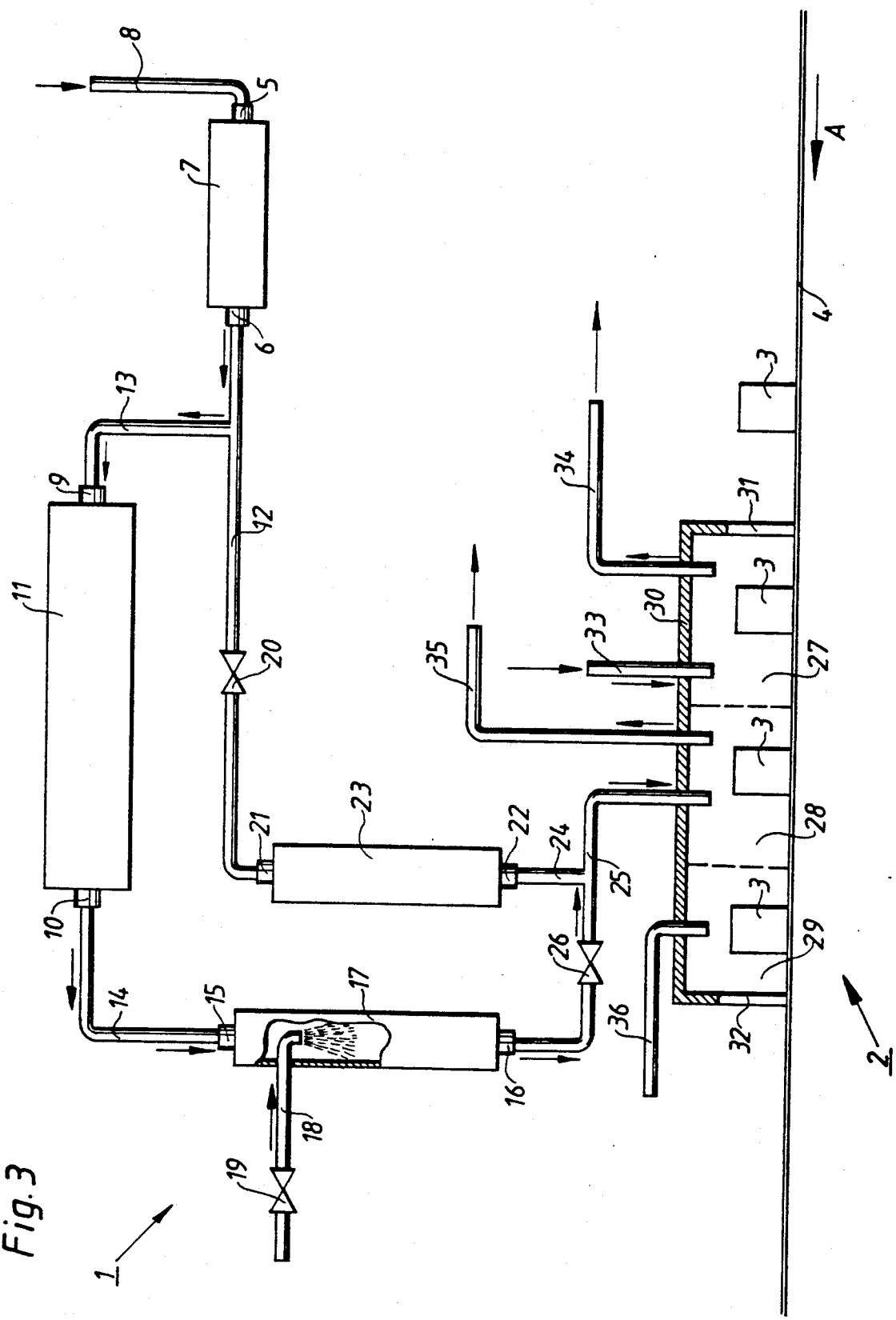

METHOD OF PRODUCING A GASEOUS HYDROGEN PEROXIDE-CONTAINING STERILIZATION FLUID

This application is a continuation of application Ser. No. 07/605,409, filed Oct. 30, 1990, now abandoned.

BACKGROUND OF THE INVENTION

1. Field of the Invention

The present invention relates to a method of producing a sterilization fluid, and more particularly to a method of producing a gaseous, hydrogen peroxide-containing sterilization fluid.

RELATED ART

Within packaging technology, use is often made of so-called aseptic packages for packing and transporting products which are particularly sensitive to bacterial attack and have short storage durability, for example foods and other perishable goods. The aseptic packages enjoy many advantages over other, non-aseptic packages. For example, products of the above-mentioned sensitive type may be stored with retained or insignificantly affected freshness for considerably longer storage times, and, may be stored without the need for refrigeration or an unbroken refrigeration chain, which considerably increases and in many respects improves the distribution possibilities of the products involved. Fundamentally, the aseptic packaging technology or production of aseptic packages is based on the concept that a product which has been sterilised beforehand by heat treatment or other sterilisation methods is filled into a package or container likewise sterilised or produced from a sterilised packaging material, the container being thereafter sealed. The entire filling operation is carried out in a sterile environment in order to avoid reinfection of the sterilized product. Today, such production is commonly carried out with the aid of modern, rational packaging machines of the type which, for example, both form, fill and seal the finished packages under the requisite aseptic conditions.

Using such a prior art packaging machine, single-use type aseptic packages are produced from prefabricated, creased-lined blanks of a laminated, flexible material, normally thermoplastic coated paper formed with one or more additional layers of other materials than The blank is first formed into an open, tubular (normally square) carton which is thereafter given a liquid-tight bottom seal by folding and sealing together of end portions of the carton forming its bottom. After the bottom sealing, which most generally takes place in stages on a path along which cartons are moved stepwise, the bottom-fitted cartons are introduced in the upright state into a sterilization and filling zone aseptically screened-off from the ambient surroundings, for sterilization and thereafter filling and sealing in a sterile atmosphere to form finished, aseptic packages for further distribution.

Using another prior art packaging machine, similar aseptic packages are produced in fundamentally the same manner as that described above, with the only differences being that the tubular cartons are first provided with an injection moulded plastic seal serving as the top seal for the finished package at the one end of the carton, and that the cartons thus end-sealed are thereafter sterilized, filled and bottom-sealed in the "upside-down" position. One example of a package produced in accordance with the first-described production principle is the Tetra Rex (Registered Trademark), while one example of a package produced in accordance with the latter production principle is the Tetra Top (Registered Trademark).

Irrespective of whether the packages are produced according to the former or latter production principles, use is normally made of a gaseous, hydrogen peroxide-containing sterilization fluid for sterilizing the bottom-sealed or top-sealed package cartons, since a gaseous sterilization fluid may, in comparison with a corresponding liquefied fluid, more readily penetrate into and sterilize concealed spaces of the cartons, for example folds formed as a result of the folding operation in the bottom seal of the cartons. At the same time, gaseous fluid is easier to ventilate off after sterilization is completed and prior to the filling operation. Furthermore, the gaseous sterilization fluid enjoys the advantage that it wholly eliminates the risk of so-called edge-absorption in the cut edges of the cartons which show a ready tendency to suck up liquid and thereby render complete driving-off of the hydrogen peroxide more difficult if not impossible. In order to preclude the risk of leaving residual amounts of hydrogen peroxide in the cartons due to such edge absorption, it is crucial that the gaseous sterilization fluid be kept, throughout the entire sterilization process, at a temperature which exceeds the dewpoint of the hydrogen peroxide, i.e., approximately 70° C. This implies that the package cartons must be heated to and kept at a temperature well above this dewpoint, normally approximately 80° C., on contact with the sterilization fluid in the sterilization zone.

An efficient hydrogen peroxide-containing sterilization gas which is employed in sterilization of packaging materials or package cartons for producing aseptic packages consists of an air/hydrogen peroxide mixture heated to approximately 120° C. and containing approximately 25 g of hydrogen peroxide per 1 kg of air. After a very brief sterilization time, of the order of 1 second, such a mixture gives a sterilization result which fully satisfies the sterilization requirements placed on aseptic packages.

A gaseous, hydrogen peroxide-containing sterilization fluid of the above-considered type is produced, according to one prior art method, by spraying finely-dispersed, liqueform hydrogen peroxide onto a heated metal surface for vaporization of the hydrogen peroxide, and then combining and by mixing the vaporized hydrogen peroxide with a regulated, heated air current. This prior art method, which utilizes heat transfer from a solid surface to the liquefied hydrogen peroxide, results in the metal surface being gradually coated with impurities, for example stabilizers normally employed in liquified hydrogen peroxide which, at high temperatures, act as catalysts for hydrogen peroxide degradation and contribute to a portion of the hydrogen peroxide being degraded and destroyed on vaporization.

However, the problem inherent in "catalytic" degradation of hydrogen peroxide may be avoided by instead carrying out the vaporization of the liquefied hydrogen peroxide using heated air as the heat transfer medium, and one prior art method which operates according to this vaporization principle is based on the concept that the air intended for the vaporization process is heated by heat exchange with a heating body heated electrically or by other means prior to the mixing operation with the liquefied hydrogen peroxide injected into the heated air current. This prior art method results in a gaseous hydrogen peroxide-containing sterilization fluid with good sterilization capability as long as it is carried out continuously, i.e. without any recurring interruptions. On the other hand, it has proved to function less satisfactorily—or defy problem-free execution—in those cases when, for one reason or another, it has been desirable to discontinue production from time to time for recurring downtimes of longer or shorter duration. As a rule, the sterilization gas produced by intermittent vaporization of the liqueform hydrogen peroxide has displayed extreme temperature variations and, hence, varying sterilization capability, which has occasionally even been so poor that it has proved difficult or impossible to meet the requisite sterilization standards. In order to ensure the desired sterilization result in sterilization of, for instance, package cartons which are to be filled with sterile contents, it has hitherto been a matter of necessity or expediency to produce the gaseous sterilization fluid continuously throughout the entire sterilization process, which has entailed that, for example, the fluid produced during the interval between carton sterilizations is wasted. By the same token, the fluid produced continuously during the ventilation of the sterilized cartons has also constituted an unnecessary excess production and an economic loss factor.

OBJECTS AND SUMMARY OF THE INVENTION

One object of the present invention is, therefore, to provide a method for producing a gaseous hydrogen peroxide-containing sterilization fluid by vaporizing liquefied hydrogen peroxide using heated air as the vaporization agent, which can be carried out intermittently while retaining good sterilization properties in the intermittently produced fluid.

A further object of the present invention is to provide a method of producing a gaseous hydrogen peroxide-containing sterilization fluid which can be used to sterilize subsequently conveyed package cartons or other objects without any part of the produced sterilization fluid becoming superfluous and going to waste.

The above objects as well as other objects not specifically enumerated are accomplished by a method of producing a gaseous, hydrogen peroxide-containing sterilization fluid in accordance with the present invention. The method of producing a gaseous, hydrogen peroxide-containing sterilization fluid in accordance with the present invention includes forming an air current, heating the air current to a substantially constant, elevated vaporization temperature, and intermittently vaporizing liquefied hydrogen peroxide in the heated air current in a manner such that the heated air current acts as a vaporization agent for the liquefied hydrogen peroxide.

BRIEF DESCRIPTION OF THE DRAWINGS

The preferred embodiments of the present invention will be described in greater detail with reference to the accompanying drawings, wherein like members bear like reference numerals and wherein:

FIG. 3 is a schematic view of the system of FIG. 1, during sterilization of a second object.

DETAILED DESCRIPTION

Figure 1:
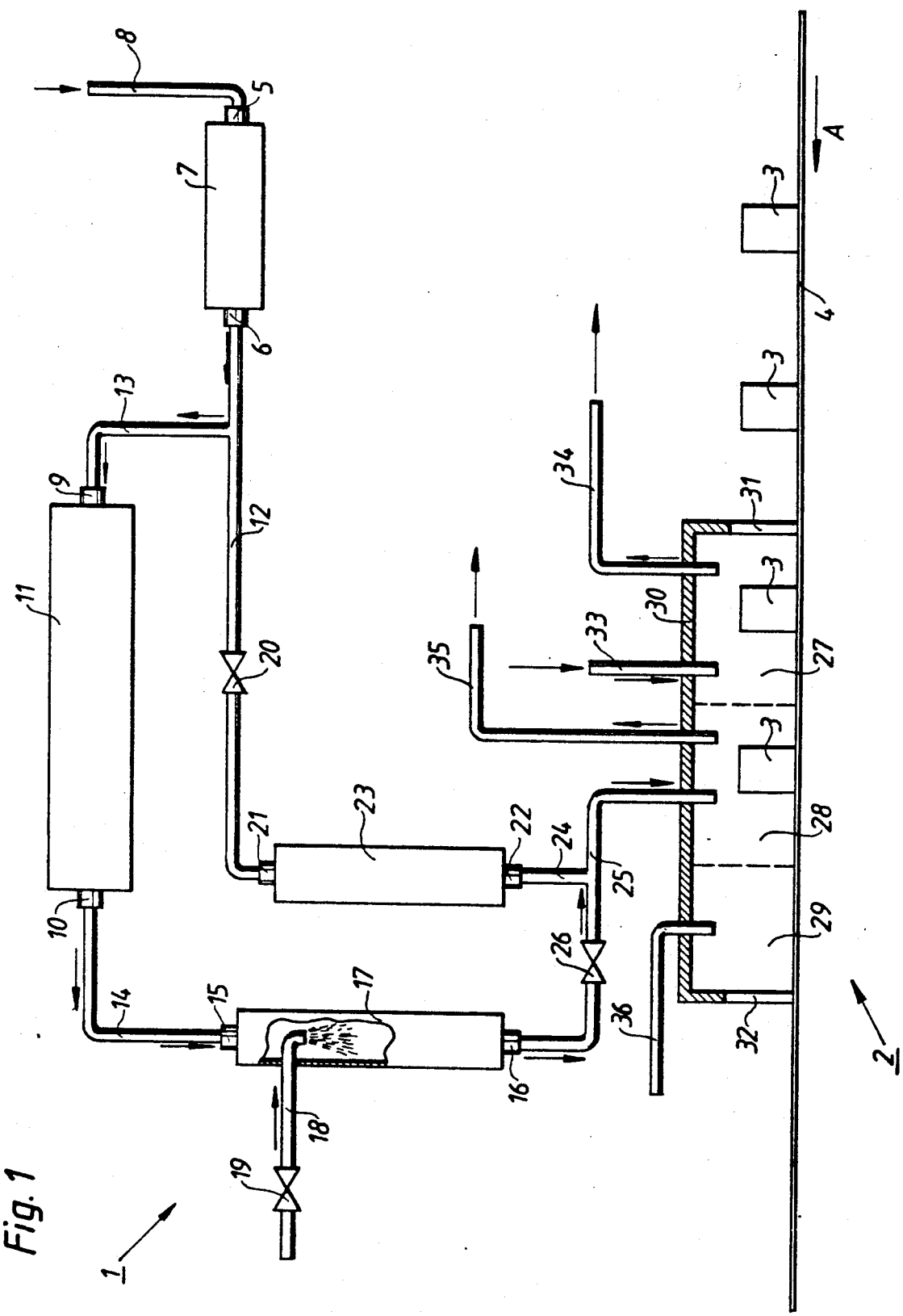
FIG. 1 is a schematic view of a system which includes an apparatus for producing a gaseous, hydrogen peroxide-containing sterilization fluid in accordance with the present invention, during sterilization of an object.
Figure 2:
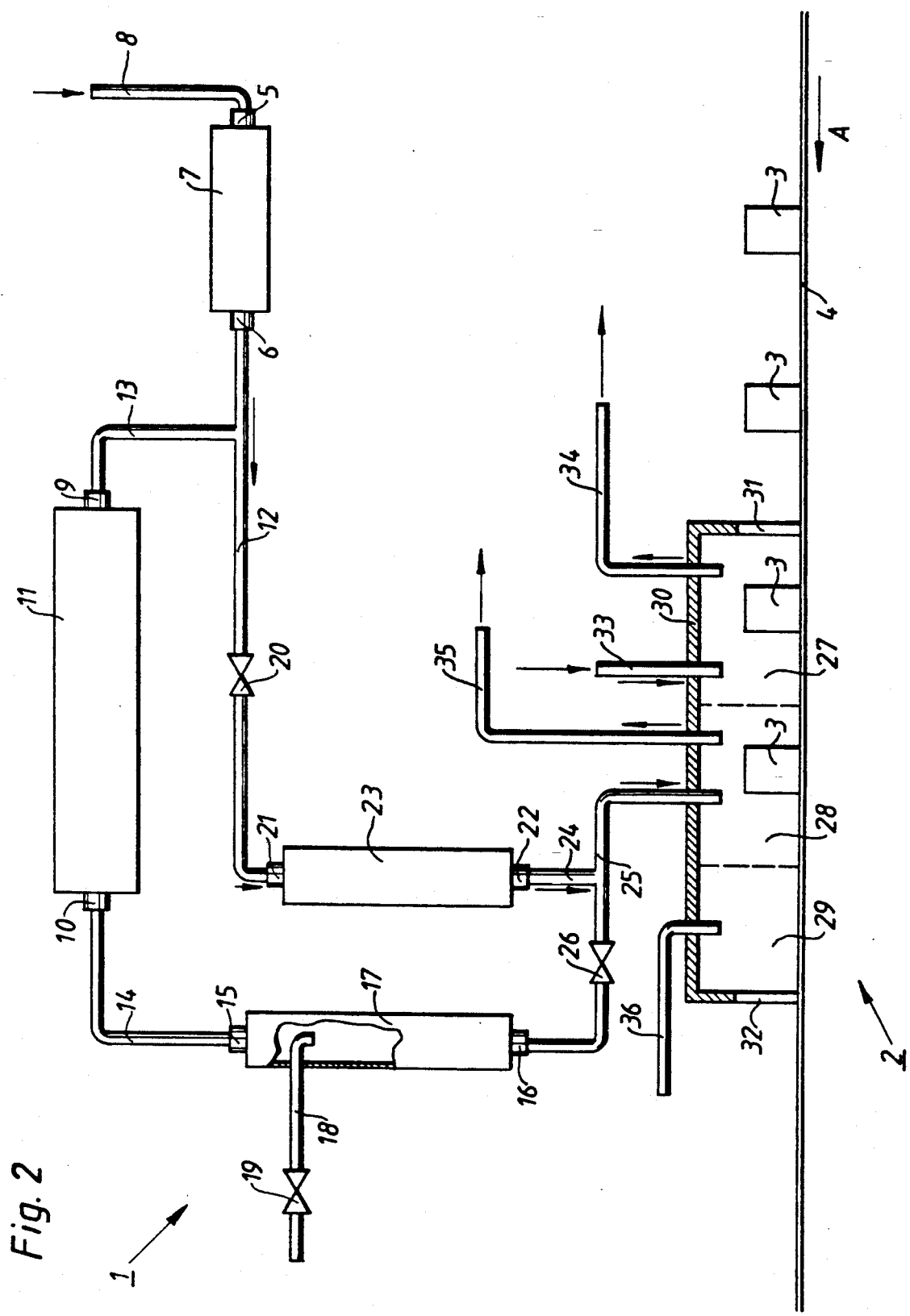
FIG. 2 is a schematic view of the system of FIG. 1, during an interruption in sterilization.

With reference to FIGS. 1-3, an apparatus for intermittent production of a gaseous, hydrogen peroxide-containing sterilization fluid is generally denoted by the reference numeral 1, and an apparatus for sterilizing objects 3 which are conveyed in mutual sequence on a conveyor belt 4 intermittently driven in the direction of the arrow A is generally denoted by the reference numeral 2. The objects 3 may, for instance, be package cartons which are intended, after sterilization to be filled with sterile contents and thereafter sealed under aseptic conditions for the formation of so-called aseptic packages. While this description will hereinafter refer to the sterilization of such package cartons, this should not be perceived as a restriction of the present invention which, in its broad scope, may naturally just as well be employed for the sterilisation of any other type of object which is to be sterilized under intermittent conditions.

The apparatus 1 includes a preheater 7 provided with an inlet 5 and an outlet 6, the preheater being in communication, via the inlet 5, with a conduit 8 for incoming filtered air. The preheater 7 is connected to a heat exchanger element 11 fitted with an inlet 9 and outlet 10, respectively, and the inlet 9 is in communication, via a conduit 13, with a conduit 12 connected to the outlet 6 of the preheater 7. A conduit 14 leads from the outlet 10 of the heat exchanger element 11, and is connected to the inlet is of a vaporization chamber 17 fitted also with outlet 46. A pipe 18 discharges into the vaporization chamber for regulated supply (with the aid of a valve 19 in the pipe 18) of liquefied preferably finely-dispersed hydrogen peroxide.

The conduit 12 connected to the outlet 6 of the preheater 7 is further connected, through an intermediary adjustable valve 20, to the inlet of a sterile filter unit 23 fitted with an inlet 21 and outlet 22. The sterile filter unit 23 is in communication, through a conduit 24 connected to the outlet 22, with a conduit 25 which is connected to the outlet 16 of the vaporization chamber 17 and which is provided with an adjustable valve 26 between the outlet 16 of the vaporization chamber and the communication with the conduit 24.

According to the present invention, the heat exchanger element 11 has a large mass (thermal capacity) and a large heat exchange surface area, and may, for instance, consist of aluminium or other material of superior thermal capacity with a capability of storing large volumes of thermal energy. The heat exchange surface of the heat exchanger 11 is kept at the desired uniform, elevated temperature by regulated heating of its large mass, either electrically or by other means, for example by superheated steam in a known manner.

The apparatus 2 comprises a housing 30 divided up into discrete chambers or zones 27-29, the housing being provided with an inlet 31 and outlet 32 of the gate type for intermittent conveyance of the package cartons 3 stood on end on the conveyor belt 4 in sequence through the chambers or zones 27-29 in the housing 30.

The chamber 27 has an inflow pipe 33 and outflow pipe 34 for the throughflow of hot fluid, e.g. air, for heating the package cartons 3, while the chamber 28 is connected to the conduit 25 of the unit 1 and is provided with an outflow pipe 35 for making possible a throughflow of fluids necessary for the sterilization process.

The chamber 29 is provided with a filler pipe 36 discharging therein for filling sterile contents into the sterilized package cartons. A suitable device (not shown) is further provided in the chamber 29 for aseptic sealing of the filled package cartons prior to discharge through the gate outlet 32.

Gaseous, hydrogen peroxide-containing sterilization fluid for sterilizing package cartons 3 is produced, in accordance with the present invention, as follows. During the sterilization (FIG. 1) of a package carton 3 fed into the sterilization chamber 28, the valve 20 in the conduit 12 is closed, while the other valves included in the system, i.e. valves 19 and 26, are open. Filtered air incoming through the conduit 8 is preheated in the preheater 7 to approximately 90° C. and is led via the conduit 13 into the heat exchanger element 11 where it is brought into contact with the heat exchange surface heated to approximately 400° C. for heating to the desired elevated vaporization temperature, of the order of 360° C. The heated air is then withdrawn from the heat exchanger element 11 through the outlet 10 and is led through the conduit 14 into the vaporization chamber 17 for intermingling with and vaporization of the liquefied hydrogen peroxide fed in finelydispersed form through the conduit 18, for the formation of the finished gaseous, hydrogen peroxide-containing sterilization fluid at the desired uniform or insignificantly varying temperature which thereby possesses good, uniform sterilization properties. The sterilization fluid, which is at a temperature of approximately 120° C. and has a hydrogen peroxide content corresponding to approximately 25 g of hydrogen peroxide per kg of supplied air, is withdrawn from the vaporization chamber 17 and led via the conduit 25 into the sterilization chamber 28 for sterilization of the above-mentioned package carton 3. Spent sterilization fluid is continuously removed from the chamber 28 through the outflow pipe 35 throughout the entire sterilization period. After completed sterilization (FIG. 2), which takes roughly 1 second, the supply of liquified hydrogen peroxide is arrested, in that the valve 19 in the conduit 18 is closed, at the same time as communication between the vaporization chamber 17 and the sterilization chamber 28 is broken by closure of the valve 26 in the conduit 25. The valve 20 in the conduit 12 is opened, whereby the air heated to approximately 90° C. in the preheater 7 is allowed into the sterile filter unit 23 in which it is caused to pass through a sterile filter of known type for separation of any micro-organisms which may possibly be present in the air. The filtered air is withdrawn from the sterile filter unit 23 through the conduit 24 and is introduced, via the conduit 25, into the chamber 28 for ventilation and driving-off of residual sterilization fluid after the sterilization process proper, through the outflow pipe 35. The ventilation continues for approximately 0.5 seconds, whereafter the sterilized and ventilated package carton 3 is displaced by means of the conveyor belt 4 into the chamber 29 for filling with sterile contents through the filler pipe 36 (FIG. 3). During this displacement, the immediately subsequent package carton 3 preheated in the chamber 27 is conveyed simultaneously into the sterilization chamber 28, and the above-described sterilization and ventilation cycle is repeated in that the valve 20 in the conduit 12 is closed and the valves 19 and 26 in the conduit 18 and the conduit 25, respectively, are opened for the supply of gaseous sterilization fluid, freshly produced in the vaporization chamber 17, to the chamber 28. The procedure is thereafter accordingly repeated in sequence for the remaining package cartons on the conveyor belt 4 which conveys the cartons through the housing 30 in synchronization with the above-mentioned sterilization and ventilation in the chamber 28 and subsequent aseptic filling and sealing in the chamber 29 for the formation of finished aseptic packages progressively discharged through the gate outlet 32.

Given that the heat exchanger element 11 has large thermal capacity and large mass, respectively, the energy supplied for heating the heat exchange surface of the heat exchanger element may be discontinued or regulated during the above-described ventilation period without any risk of undesirable cooling of the heat exchange surface or excessive heating of the air waiting in the heat exchanger element, since the heat exchange surface will, during the discontinued or regulated supply of energy, be reliably maintained at the desired even temperature by heating from the heat stored in the heat exchanger element. It will thereby be ensured in the method according to the present invention that the air heated in the heat exchanger element is kept at a constant or in any event insignificantly varying vaporization temperature when it departs from the heat exchanger element and is fed into the vaporization chamber 17, even if production of the gaseous, hydrogen peroxide-containing sterilization fluid were to be carried out with very frequently recurring interruptions, be they brief or lengthy, in the supply of the liquefied hydrogen peroxide.

Thus, according to the present invention it is possible, employing simple, easily regulated equipment, to produce a gaseous, hydrogen peroxide-containing sterilization fluid at an ensured uniform or insignificantly varying temperature with good stable sterilization properties for efficient sterilization of package cartons or other intermittently conveyed objects, without any part of the produced fluid going to waste.

While this invention has been illustrated and described in accordance with a preferred embodiment, it is recognized that variations and changes may be made therein without departing from the invention as set forth in the claims.

What is claimed is:

1. A method for conducting sterilization by an air stream containing hydrogen peroxide, comprising:
   (a) heating a stream of ambient air in a preheater to a temperature of about 90° C.;
   (b) conducting the heated air stream intermittently through a first conduit and into a heat exchanger to increase the temperature of the heated air stream to a hydrogen peroxide vaporizing temperature;
   (c) injecting liquefied hydrogen peroxide into the hydrogen peroxide-vaporizing air stream such that the hydrogen peroxide-vaporizing air stream vaporizes all of the liquefied hydrogen peroxide resulting in an air and vaporized hydrogen peroxide stream and supplying the air and vaporized hydrogen peroxide stream into a third conduit and then into a chamber for sterilizing the contents of the chamber; and
   (d) reducing flow through said first conduit and conducting the heated air stream intermittently through a second conduit and into said third conduit and then into said chamber for drying the contents of the chamber, the flow of said heated air stream in said first conduit alternating with the flow of said heated air stream in said second conduit.

2. The method according to claim 1, including filtering the heated air stream in the second conduit, and wherein the heated air stream in the second conduit is at a temperature of about 90° C.

3. The method according to claim 1, wherein said injecting step produces a concentration of hydrogen peroxide in the hydrogen peroxide-vaporizing air stream of about 25 grams of hydrogen peroxide per kilogram of air.

4. The method according to claim 1, wherein the intermittent flow of the heated air stream in the first conduit has a duration of about one second and the intermittent flow of the heated air stream in the second conduit has a duration of about 0.5 seconds.

5. An apparatus for sterilizing articles in a chamber, comprising:

(a) a first conduit for receiving ambient air and forming an air stream; preheater means in said first conduit for heating said air stream;

(b) an outlet conduit for conducting said air stream into a chamber;

(c) a second conduit communicating between said preheater means and said outlet conduit, said second conduit including valve means for controlling flow through said second conduit;

(d) a third conduit communicating between said preheater means and said outlet conduit, said third conduit including valve means for controlling flow through said third conduit, said third conduit also including heat exchange means for heating the air stream to a temperature sufficient to vaporize liquefied hydrogen peroxide and vaporization means for vaporizing liquid hydrogen peroxide, and means, associated with the vaporization means, for injecting liquefied hydrogen peroxide into the vaporization means such that the heated air stream vaporizes all of the injected liquefied hydrogen peroxide; and (e) means for alternately opening said valve means in said second conduit and in said third conduit, whereby the air stream containing hydrogen peroxide flows intermittently into said chamber to sterilize articles in said chamber, and whereby the air stream through the second conduit flows intermittently into said chamber to dry articles in the chamber.

6. The apparatus according to claim 5, wherein said heat exchange means including a heat exchange element having a large thermal capacity and large surface area.

* * * * *